(12) United States Patent
Conti et al.

(10) Patent No.: US 8,653,136 B2
(45) Date of Patent: *Feb. 18, 2014

(54) COMPOSITIONS BASED ON AMINO ACIDS FOR IMPROVING THE MYOCARDIAL VENTRICULAR FUNCTION IN PATIENTS SUFFERING FROM DIABETES

(75) Inventors: Franco Conti, Milan (IT); Francesco Saverio Dioguardi, Milan (IT)

(73) Assignee: Determinants of Metabolism Research Laboratory S.R.L., Castel San Griovanni (IT)

( * ) Notice: Subject to any disclaimer, the term of this patent is extended or adjusted under 35 U.S.C. 154(b) by 1186 days.

This patent is subject to a terminal disclaimer.

(21) Appl. No.: 12/104,722

(22) Filed: Apr. 17, 2008

(65) Prior Publication Data

US 2008/0194665 A1    Aug. 14, 2008

Related U.S. Application Data

(62) Division of application No. 10/480,774, filed as application No. PCT/IB02/02149 on Jun. 10, 2002, now abandoned.

(30) Foreign Application Priority Data

Jun. 15, 2001   (IT) .................................. TO01A0580

(51) Int. Cl.
| | |
|---|---|
| *A61K 31/198* | (2006.01) |
| *A61K 31/405* | (2006.01) |
| *A61K 31/4172* | (2006.01) |
| *A61P 9/00* | (2006.01) |
| *A61P 3/10* | (2006.01) |

(52) U.S. Cl.
USPC ........... 514/561; 562/575; 562/562; 562/570; 562/443; 562/445; 562/559; 562/557

(58) Field of Classification Search
USPC .......... 514/561; 562/575, 562, 570, 443, 445, 562/559, 557
See application file for complete search history.

(56) References Cited

U.S. PATENT DOCUMENTS

| | | | |
|---|---|---|---|
| 4,053,589 A | 10/1977 | Gans et al. | |
| 5,032,608 A * | 7/1991 | Dudrick | 514/396 |
| 5,132,113 A * | 7/1992 | Luca | 424/750 |
| 6,218,420 B1 * | 4/2001 | Dioguardi | 514/419 |
| 7,902,250 B2 * | 3/2011 | Dioguardi | 514/419 |

FOREIGN PATENT DOCUMENTS

| | | | |
|---|---|---|---|
| EP | 0483614 | * | 5/1992 |
| JP | 60-255722 | | 12/1985 |
| WO | WO 98/26774 | | 6/1998 |

OTHER PUBLICATIONS

Vekshetein et al (Circulation, 1990, 82, 2068-74.*
Wright, "Amino acids in the treatment of ischaemic heart disease", Journal of Molecular and Cellular Cardiology, 17(5), pp. 441-443 (1985).*

* cited by examiner

*Primary Examiner* — Sreeni Padmanabhan
*Assistant Examiner* — Irina Neagu
(74) *Attorney, Agent, or Firm* — Sughrue Mion, PLLC

(57) ABSTRACT

Compositions based on amino acids are described, for improving the myocardial ventricular function in patients suffering from diabetes, particularly but not exclusively II type diabetes. The compositions according to the invention comprise up to 75% of the branched chain amino acids leucine, isoleucine and valine, as active ingredients. Preferably, the compositions also comprise, as further active ingredients, up to 50% of threonine and lysine. Other essential amino acids are preferably also provided, in particular methionine, phenylalanine, histidine, tryphtophan, as well as non essential amino acids, in particular tyrosine and/or cyst(e)ine (i.e., cystine and cysteine). Other amino acids can be added, provided that their sum is in a percentage being lower than 20% with respect to the other active ingredients, and less than 10% for each single amino acid.

7 Claims, No Drawings

COMPOSITIONS BASED ON AMINO ACIDS FOR IMPROVING THE MYOCARDIAL VENTRICULAR FUNCTION IN PATIENTS SUFFERING FROM DIABETES

This is a divisional of application Ser. No. 10/480,774 filed Dec. 15, 2003 now abandoned, which is a §371 of PCT Application No. PCT/IB02/02149 filed Jun. 10, 2002, claiming priority from Italian Patent Application Number TO2001A000580, filed on Jun. 15, 2001. The entire disclosures of the prior applications, application Ser. Nos. 10/480, 774 and PCT/IB02/02149 is considered part of the disclosure of the accompanying divisional application and is hereby incorporated by reference.

The present invention refers to compositions based on amino acids for improving the myocardial ventricular function in patients suffering from diabetes, in particular II type diabetes.

Experimental studies carried out on patients of the indicated type have shown, at myocardium level, a depression of the energetic metabolism, a reduction of the synthesis velocity and an increase of the proteins degradation. A general degradation of the mechanical function of the cardiac muscle derives from the above, whose main pathogenic mechanisms are the reduced availability of energetic material and the presence of contractile proteins having low ATPhase activity.

At present, no therapeutic approaches are known aimed at producing a noticeable improvement of the ventricular myocardial function in patients suffering from diabetes, in order to favorably influence the natural story of said patients, by retarding or preventing the appearance of cardiac insufficiency, which represents the main cause of morbidity and mortality within said population of patients.

The present invention has the aim of indicating an absolutely innovative therapeutic approach to the above mentioned problem.

Within this frame, a first aim of the invention is that of indicating compositions capable of determining a noticeable improvement of the myocardial ventricular function in patients suffering from diabetes, particularly but not exclusively II type diabetes.

A further aim of the invention is that of indicating compositions capable of determining, in patients of the above type, a noticeable increase of the ventricular ejection fraction, at rest and at peak of the isometric exercise.

A further aim of the invention is that of indicating compositions capable of eliminating the reduction of the ventricular ejection fraction which, in patients suffering from diabetes, occurs during isometric strain.

The inventors arrived at the formulation of compositions based on amino acids, as per the enclosed claims which are an integral part of the present description, which prove to be particularly effective for the proposed purposes.

Said compositions, being provided either for oral and parenteral use, are characterized by comprising, as main active ingredients, the branched chain amino acids leucine, isoleucine and valine, up to 75% of all the amino acids or active ingredients being present, by expressing the value in molecular weights.

Preferably, the compositions according to the invention also comprise, as further active ingredients, threonine and/or lysine, where in particular threonine plus lysine are present up to 50% of all the amino acids or active ingredients being present, by expressing the value in molecular weights.

In case, the compositions can provide for, as further active ingredients, other essential amino acids, in particular methionine and/or phenylalanine and/or histidine and/or tryphtophan, and non essential amino acids, in particular tyrosine and/or cyst(e)ine (i.e. cystine and cysteine).

Preferably, the sum of the amounts expressed in molecular weights of threonine and lysine is greater than the sum of the single amounts of the other essential amino acids being provided, but in any case lower than the sum of the single amounts of the branched chain amino acids being provided. In addition, the amounts expressed in molecular weight of threonine and of lysine can be each greater than the single amounts of the other essential amino acids being provided, but in any case lower than the single quantities of the branched chain amino acids being provided.

The compositions according to the invention can also comprise one or more further amino acids, with respect to those as previously indicated, the sum of which, expressed in molecular weight, is preferably lower than 20% with respect to the active ingredients, and less than 10% for each single further amino acid.

It should be noticed that, in general terms, a mixture of amino acids particularly suitable for nutritional use in humans should satisfy different requirements:

the pH of the solution of the mixture should be substantially neutral, in order to prevent urinary calcium losses;

the mixture should be safe, in respect to calcium balance (i.e.: with no urinary losses) and homocyst(e)ine production (i.e., preferably related to the amount of all amino acids, a strictly correct ratio of sulphur containing amino acids, with a ratio cyst(e)ine/methionine of at least 2:1 on a stoichiometric basis).

In addition, the content of essential amino acids in the mixture should be preferably in an adequate ratio to fulfill real human nutritional needs (and this can be optimized by the co-operative adjunction of adequate and small ratios of some non essential amino acids).

Within this frame, a preferred formulation of the compositions according to the invention, comprising essential amino acids (leucine, isoleucine, valine, threonine, lysine, methionine, phenylalanine, histidine, tryphtophan) and some non essential amino acids (tyrosine and cyst(e)ine), in different but fixed and co-operative molar ratios among them, is the following one:

branched chain amino acids leucine (40-60% in molecular weight), isoleucine (20-40% in molecular weight) and valine (20-40% in molecular weight), preferentially in a stoichiometric ratio 2:1:1 among them, covering from 30 to 60% of the weight of the whole mixture;

threonine plus lysine, preferably in a molar ratio with the said branched chain amino acids between 20 and 50%, preferably in a threonine to lysine ratio in which lysine is from 10 to 50% more represented than threonine;

the above said branched chain amino acids plus threonine and lysine, whose sum of the molecular weight is in a stoichiometric ratio of 50 to 70% of a mixture also comprising histidine and other amino acids, were histidine is present in molar fraction up to 50% of the following amino acids:

cyst(e)ine (i.e., cystine and cysteine) and methionine, up to 50% of histidine (the ratio between cyst(e)ine and methionine should be preferably of 50 to 200% greater for cyst(e)ine in molar ratio), phenylalanine and tyrosine, in molar ratio up to 50% of histidine (in which tyrosine is preferably represented up to 50% of the molar weight of phenylalanine), tryphtophan, up to 10% of the weight of all the other amino acids, on a molar weight basis.

It has to be noticed that any other amino acid can be added to the above formulation, without altering the expected effects, provided that the sum of the additional amino acids is in a percentage lower than 20% with respect to the other active ingredients (less that 10% for each single amino acid).

It should also be noticed that a significant characteristic of the above said formulation is that of having a pH in water solution comprised between 6.5 and 8.5, and therefore suitable for a safe oral or parenteral use, in humans or animals, according to needs. This feature prevents the excessive calcium urinary losses induced by protein sources of amino acids.

The effects of an amino acids mixture according to the above suggested formulation were the subject of a comparative study.

To this purpose, 18 patients suffering from II type diabetes mellitus were recruited (M/F 16/2, age 62±6 years, body mass index (BMI) 27.4±3.0 kg/m$^2$). The average duration of the disease was 12±8 years. Glycate haemoglobin was 8.2±0.8%. After the basal evaluation, patients were randomized at the treatment with a composition of amino acids according to the above said preferred formulation of the invention (12 g/die) or with placebo, for a period of 3 weeks. The treatment was subsequently exchanged and maintained for a further period of 3 weeks.

The analyzed main metabolic parameters were: glycaemia, insulinemia, C-peptide, free fatty acids (FFA), total and fractioned cholesterol, triglycerids and fibrinogen.

The left ventricular function was evaluated by means of 2D echocardiography, using a Hewlett-Packard Sonon 5500 system, with dedicated program for the execution of echo-stress methodologies and the quantification of ventricular images. The echocardiographic studies were encoded and blind analyzed, by two independent observers, without knowing the identity of the patient and the experimental condition. The echocardiographic analysis was carried out using a digital cine-loop method (Prevue System, Nova Microsonics Inc.). The ventricular volumes were calculated, in the various experimental conditions, with a biplane area-length method, from which the ejection fraction (EF) was derived as index of ventricular pump function: EF=VTD–VTS/VTD, wherein VTD and VTS represent the telediastolic and telesistolic volume of the left ventricle, respectively.

The parietal contractile function was evaluated by analyzing the myocardium sistolic thickening, in each segment obtained by subdividing the left ventricle into 16 segments (according to the American Society of Echocardiography standards) and by using a semiquantitative score system (1=normal, 2=hypocinesia, 3=akinesia, 4=dyscinesia).

The general and regional ventricular function was studied at rest conditions and during isometric strain through handgrip test.

After having determined the maximal voluntary contraction by means of a dynamometer, an isometric strain at 40% was carried out for 3 minutes. During strain, ventricular function was monitored by 2D echocardiography and the arterial pressure was monitored through a continuous oscillometric method (Nippon Colin Co. Ltd).

The results of the study are expressed as mean±SD. The multiple comparisons were carried out by means of the two-way variance analysis for repeated measures, followed by the Fisher's test. A two-tailed value ≤0.05 as been considered as a significant one.

None of the metabolic parameters was significantly modified, neither by the treatment with the amino acids mixture according to the invention, nor by the administration of placebo.

As it is apparent from Table 1 which follows, the treatment with the mixture according to the invention did not brought to significant variations, concerning glycaemia at fast, insulinemia and sensitivity to insulin considered through the insulin tolerance test technique.

Also concerning lipidic metabolism, no variations were observed in relation to total cholesterol, HDL, triglycerids, free fatty acids and Lp(a). In addition, no substantial modifications occurred concerning both pressure values and body mass index.

TABLE 1

Clinical characteristics of patients

|  | Placebo | Invention | P |
|---|---|---|---|
| Demography |  |  |  |
| Age (years) | 62 ± 6 |  |  |
| Clinical characteristics |  |  |  |
| Disease duration (years) | 10 ± 7 |  |  |
| Body mass index (SD) (kg/m$^2$) | 27 ± 3 | 27 ± 3 | n.s. |
| Anti-hypertension treatment (%) | 77% |  |  |
| Sistolic pressure (SD) (mm Hg) | 151 ± 12 | 154 ± 17 | n.s. |
| Diastolic pressure (SD) (mmHg) | 84 ± 5 | 84 ± 6 | n.s. |
| HbA1c (SD) (%) | 8.7 ± 1.7 | 8.6 ± 1.6 | n.s. |
| Insulinemia (SD) (μm/ml) | 14 ± 8 | 20 ± 15 | n.s. |
| Cholesterolemia (SD) (mg/dl) | 225 ± 27 | 214 ± 24 | n.s. |
| HDL cholesterol (SD) (mg/dl) | 47 ± 13 | 46 ± 15 | n.s. |
| Triglyceridemia (SD) (mg/dl) | 165 ± 91 | 115 ± 66 | n.s. |
| Free fatty acids (SD) (μmol/l) | 699 ± 395 | 656 ± 370 | n.s. |
| Lp(a) (SD) (mg/dl) | 12 ± 10 | 13 ± 10 | n.s. |
| Proteinuria (mg/die) | 40 ± 35 | 45 ± 29 | n.s. |
| Anti-diabetes therapy (D/ADO/ADO + I/I) | 2/9/3/4 |  |  |

By analyzing the general ventricular function of the patients being the subject of the study, it was possible to draw the following conclusions:

1) the treatment with the amino acids mixture according to the invention does not modify, in a significant manner, the ventricular dimensions (considered as telediastolic volume), neither at rest (77±24 vs. 78±24 ml/m$^2$, p=ns), nor at the peak of the isometric strain (86±26 vs. 88±25 ml/m$^2$, p=ns). In addition, the same increment induced by the isometric strain is maintained;

2) during treatment with the amino acids mixture according to the invention, the ejection fraction increases in a significant manner, both at rest (58±8 vs. 52±12%, p=0.009) and at the peak of the isometric strain (58±10 vs. 43±13, p=0.0001); it is then particular interesting that 3) the reduction of the ejection fraction during isometric effort is abolished, with respect to the basal condition (p=0.188), which is instead maintained during placebo (p<0.0001).

Upon analyzing the regional myocardial contractile function of the patients, the following remarks are possible:

the administration of the amino acids mixture according to the invention determines a reduction of the extension of the regional contractile dysfunction at rest (considered as wall motion score index, WMSI) (1.32±0.42 vs. 1.26±0.41, p=0.005);

the isometric strain causes an extension of the regional contractile dysfunction independently of the type of treatment, but the extension of the contractile dysfunction at the strain peak is smaller during the treatment with the amino acids mixture according to the invention (1.49±0.45 vs. 1.29±0.41, p<0.05).

It results clear from the above that the oral administration of the amino acids mixture according to the invention determines remarkable variations of the myocardial and ventricular function in diabetes patients, in particular II type diabetes.

Said administration has in fact positively influenced the left ventricular myocardial function, both at rest and during isometric strain. The fact is particularly interesting that said administration prevents the depression of the function caused by isometric strain which characterizes diabetes patients.

The above data also highlight a positive action on myocardial inotropism and contractile recruitment during conditions of increased load (such as during hand grip characterized by an acute increase of the postload). This effect can be the result of the combined action of an improvement of the energetic metabolism and an inversion of the shift of the synthesis of contractile proteins to the production of fast ATPhase activity elements.

The results deriving from the study of the regional contractile function also highlight a reduction of the extension of the reversible chronic contractile dysfunction, which is a sign of a favorable influence on hibernating myocardium.

Finally, the administration of the amino acids mixture according to the invention reduces the further extension of the contractile dysfunction induced by acute ischemia during isometric strain.

From the given description the features of the present invention are clear, as well as its advantages. In particular, the oral administration of the described mixture of amino acids positively influences the myocardial ventricular function of patients suffering from diabetes, in particular II type diabetes. The positive influence is evident either at rest and during the acute overload imposed by an isometric strain during handgrip, and also on the parietal contractile function, by means of a reduction of the extension of myocardial hibernation phenomena and of the extension of the contractile dysfunction induced by acute ischemia during isometric strain.

It results therefore clear that the proposed treatment with amino acids allows for favorably influencing the natural story of diabetic patients, by retarding or preventing the appearance of cardiac insufficiency, which represents the main cause of morbidity and mortality within said population of patients.

The invention claimed is:

1. A method for improving myocardial ventricular function in a patient suffering from diabetes, comprising administering to the patient a composition consisting essentially of leucine, isoleucine, valine, lysine, threonine, phenylalanine, tyrosine, methionine, cyst(e)ine, histidine and tryptophan,
    wherein leucine, isoleucine and valine are present in the following molar ratio:
        from 40 to 60% of leucine in molar weight,
        from 20 to 40% of isoleucine in molar weight, and
        from 20 to 40% of valine in molar weight,
in a stoichiometric molar ratio 2:1:1, the sum of the amounts of the branched chain amino acids leucine, isoleucine and valine being comprised between 30 to 60% of the weight of the whole mixture.

2. The method according to claim 1, wherein the composition is administered orally.

3. The method according to claim 1, wherein threonine and lysine are administered in a molar ratio (Mw/Mw) with said branched chain amino acids between 20 and 50%.

4. The method according to claim 1,
    wherein the sum of threonine and lysine is in a molar ratio (Mw/Mw) from 50 to 70% with histidine.

5. The method according to claim 1, wherein the cyst(e)ine is present in a molar ratio (Mw/Mw) from 50 to 200% of the amount of methionine.

6. The method according to claim 1, wherein the phenylalanine and tyrosine are present in a molar ratio of up to 50% of the amount of histidine.

7. A method for retarding or reducing the likelihood of cardiac insufficiency in a patient suffering from type II diabetes, comprising administering to the patient a composition consisting essentially of leucine, isoleucine, valine, lysine, threonine, phenylalanine, tyrosine, methionine, cyst(e)ine, histidine and tryptophan,
    wherein leucine, isoleucine and valine are present in the following molar ratio:
        from 40 to 60% of leucine in molar weight,
        from 20 to 40% of isoleucine in molar weight, and
        from 20 to 40% of valine in molar weight,
    in a stoichiometric molar ratio 2:1:1, the sum of the amounts of the branched chain amino acids leucine, isoleucine and valine being comprised between 30 to 60% of the weight of the whole mixture.

* * * * *